(12) United States Patent
McEneaney

(10) Patent No.: US 8,021,315 B1
(45) Date of Patent: Sep. 20, 2011

(54) FINGERTIP PROTECTING DEVICE

(76) Inventor: Kimberly McEneaney, Villas, NJ (US)

( * ) Notice: Subject to any disclaimer, the term of this patent is extended or adjusted under 35 U.S.C. 154(b) by 937 days.

(21) Appl. No.: 11/635,456

(22) Filed: Dec. 6, 2006

(51) Int. Cl.
*A61F 13/00* (2006.01)

(52) U.S. Cl. ........................................... 602/22

(58) Field of Classification Search .................. 219/432; 607/86; 602/22
See application file for complete search history.

(56) References Cited

U.S. PATENT DOCUMENTS

| | | | |
|---|---|---|---|
| 3,858,985 A * | 1/1975 | Fiveash | 401/2 |
| 4,198,561 A * | 4/1980 | Fujioka | 219/433 |
| 4,210,859 A * | 7/1980 | Meretsky et al. | 323/331 |
| 5,975,083 A | 11/1999 | Henderson, Jr. | |
| 5,987,645 A | 11/1999 | Teaster | |
| 6,303,910 B2 * | 10/2001 | Glucksman et al. | 219/430 |
| 6,573,481 B2 * | 6/2003 | Glucksman | 219/432 |
| 6,756,567 B1 * | 6/2004 | Suen | 219/424 |
| 6,912,728 B2 | 7/2005 | Panella | |
| 2004/0083530 A1 | 5/2004 | Le Vert et al. | |

* cited by examiner

*Primary Examiner* — Kim Lewis
(74) *Attorney, Agent, or Firm* — Norman E. Lehrer

(57) ABSTRACT

A fingertip protecting device for preventing the contact and the spread of germs includes a housing having a container and a cover. A quantity of molten wax is stored within the container and a heater for heating the wax is stored within the housing. A person's fingertip may contact the molten wax through an opening formed in the cover. The housing also includes a scraper for removing the hardened wax from the person's fingertip and a waste container into which the wax scraping may be deposited.

3 Claims, 2 Drawing Sheets

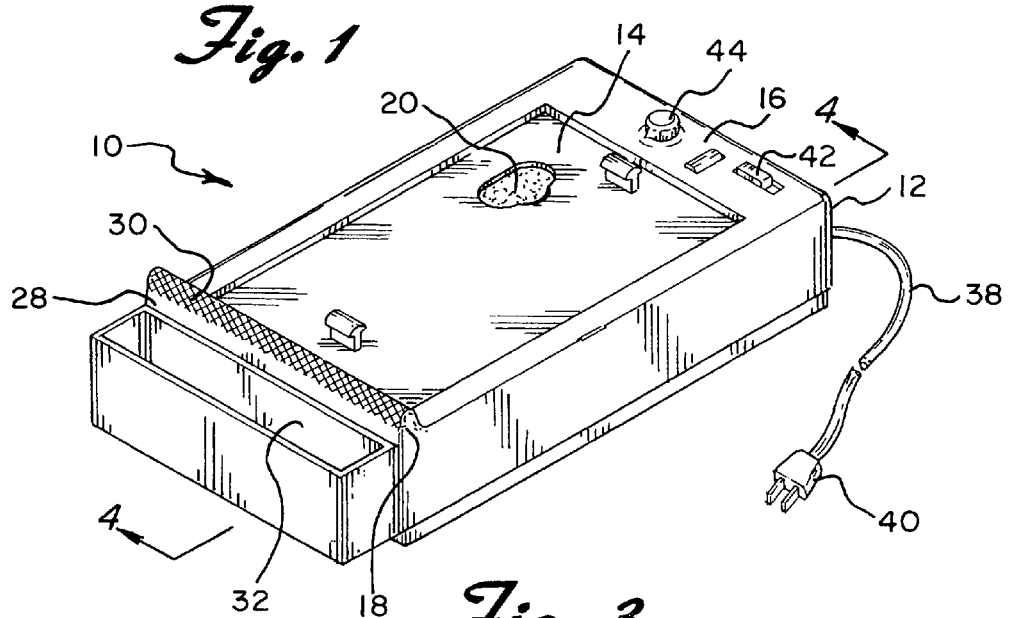
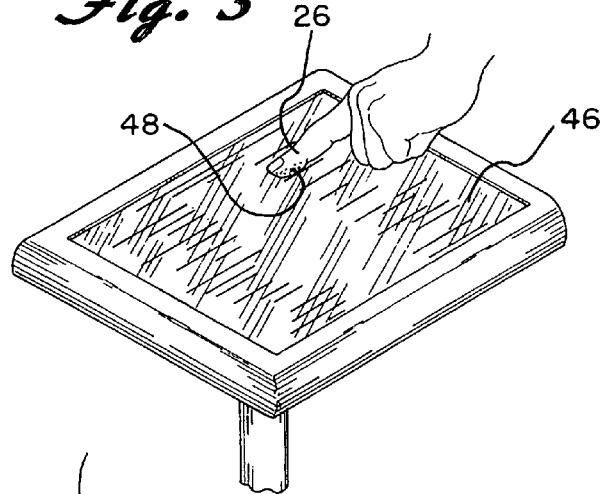
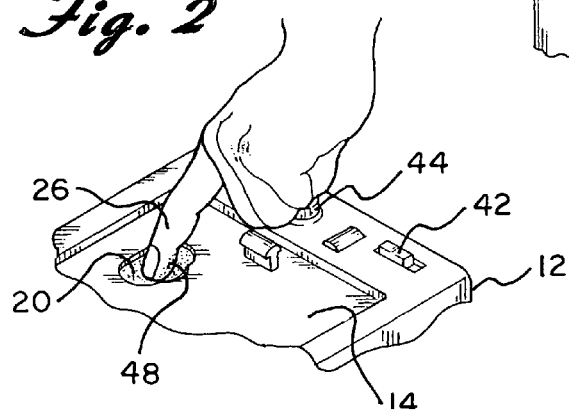

FINGERTIP PROTECTING DEVICE

BACKGROUND OF THE INVENTION

The present invention is directed toward a fingertip protection device, and more particularly, toward a device for applying a wax coating on a person's fingertips in order to prevent the contact and spread of germs when the person uses a public touch screen or keypad.

Common sources of germs are surfaces and objects that many people touch in a day. For example, doorknobs, restaurant tables, office desks, and self-service areas in convenience stores all have surfaces where germs are present and may be passed quickly and quite easily from person to person.

Today's society is very conscious about contacting germs, spreading germs, and ultimately contracting various diseases that are about. In fact, antibacterial soap and hand gel have become common household products. Hand gel is even available in a portable size so that individuals may carry a bottle with them and sanitize their hands as desired.

Another well known way to combat the contact and spread of germs is to wear disposable plastic or rubber gloves. This solution, however, may be somewhat inconvenient and burdensome to wear and use. That is, people do not normally carry such gloves with them. Also, many public places do not provide such gloves to the general public. Furthermore, some people are allergic to the material from which such gloves are made.

Various other solutions have also been proposed. For example, U.S. Pat. No. 5,975,083 to Henderson, Jr. discloses a dispenser that includes a roll of an adhesive material that has areas in the shape or form of a person's hand. The user places his or her hand on the material so that it adheres to the person's hand. The end may be cut away from the roll by a serrated edge located on the dispenser. Using the material dispensed by the device, a barrier is formed between the person's hand and whatever he or she touches. This solution, however, does not appear to be very practical and may become rather burdensome to the store owner, office or the like supplying the dispenser and material as the material may be wasted and may not be disposed of properly as people use it. This would create extra time necessary to clean up as well as an additional expense in keeping the dispenser stocked.

Also, U.S. Pat. No. 6,912,728 to Panella discloses a dispenser for housing a plurality of sanitary barrier sheets where each sheet includes a pocket for holding one or more of a person's fingertips. The barrier may be used before grasping a doorknob or the like. This device, however, may cause additional waste, expense, and maintenance for the owner of a business who wishes to make such a device available to the general public.

Therefore, a need exists for a cost efficient and simple way to prevent the spread and contact of germs in public places and particularly for those persons using a touch screen or key pad in a public place.

SUMMARY OF THE INVENTION

The present invention is designed to overcome the deficiencies of the prior art discussed above. It is an object of the present invention to provide a fingertip protecting device that protects a person from contacting germs when using a touch screen or keypad in a public place.

It is another object of the present invention to provide a fingertip protecting device that prevents the spread of germs.

It is a further object of the present invention to provide a fingertip protecting device that is efficient and simple to use.

In accordance with the illustrative embodiments demonstrating features and advantages of the present invention, there is provided a fingertip protecting device for preventing the contact and the spread of germs that includes a housing having a container and a cover. A quantity of molten wax is stored within the container and means for heating the wax is stored within the housing. A person's fingertip may contact the molten wax through an opening formed in the cover. The housing also includes means for scraping the wax from the person's fingertip and a waste container into which the wax scraping may be deposited.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings, one form that is presently preferred; it being understood that the invention is not intended to be limited to the precise arrangements and instrumentalities shown.

FIG. 1 is a front perspective view of the protecting device of the present invention;

FIG. 2 illustrates a person coating his or her fingertip with wax using the device of the present invention;

FIG. 3 illustrates a person using a touch screen after having used the device of the present invention;

DETAILED DESCRIPTION OF THE PREFERRED EMBODIMENT

Figure 4:
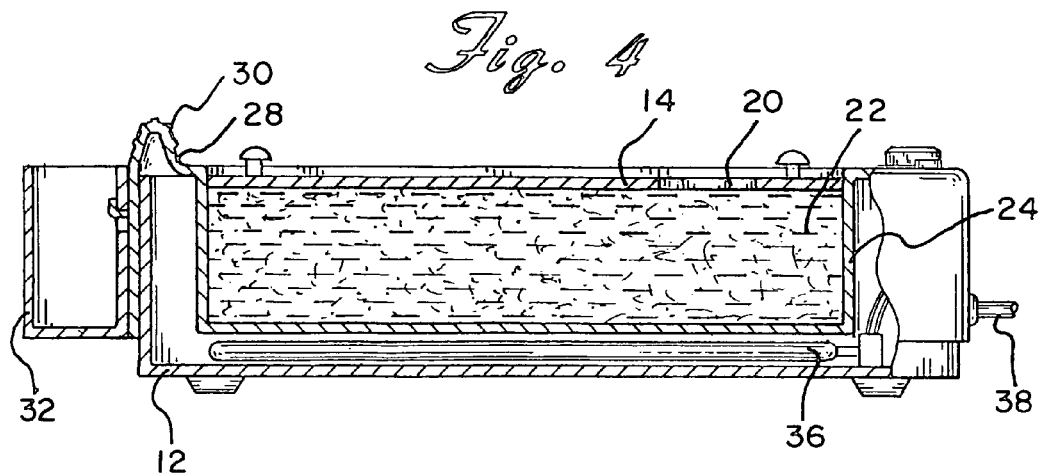
FIG. 4 is a cross-sectional view of the invention taken through line 4-4 of FIG. 1.

Referring now to the drawings in detail wherein like reference numerals have been used throughout the various figures to designate like elements, there is shown in FIG. 1 a fingertip protecting device constructed in accordance with the principles of the present invention and designated generally as 10.

Figure 5:
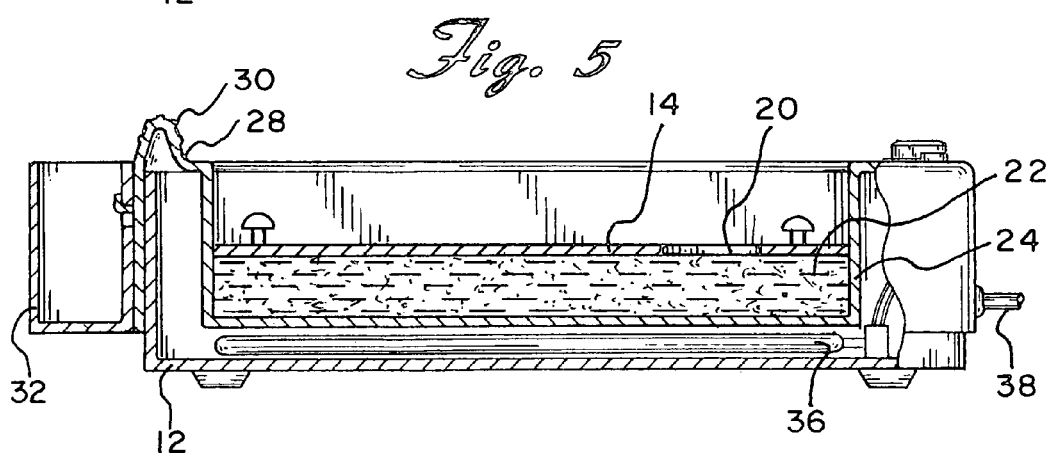
FIG. 5 is a cross-sectional view similar to FIG. 4 but illustrating the molten wax contained in the protecting device of the present invention being depleted.

The fingertip protecting device of the present invention for preventing the contact and spread of germs essentially includes a generally rectangular housing 12 having a moveable cover 14, a top end 16, and a bottom end 18. An elongated opening 20 is formed within the cover 14. A quantity of molten wax 22 is stored within the housing 12, and means for heating the wax 22 is located within or is otherwise associated with the housing 12. The wax 22 may be housed within a container 24 situated within the housing 12 with the moveable cover 14 resting on the surface of the wax 22. (See FIGS. 4 and 5.)

The housing 12 also includes a means for scraping the hardened wax from a person's fingertip 26 located adjacent the foot or bottom end 18 of the housing 12. (See FIG. 1.) The scraping means is preferably in the form of an upwardly extending flange 28 with a roughened or scored edge 30. A waste container 32 is attached adjacent the end of the housing 12 where the scraping means is located. Wax scrapings 34 may be deposited into the waste container 32 as will be described in greater detail below.

The heating means includes an electric heating element 36. (See FIG. 4.) The heating element 36 is attached to an electrical cord 38 with a plug 40 for insertion into a source of electricity. The heating element 36 is controlled by switch 42 located adjacent the top end 16 of the housing 12. The temperature of the wax may be controlled by switch 44.

Figure 6:
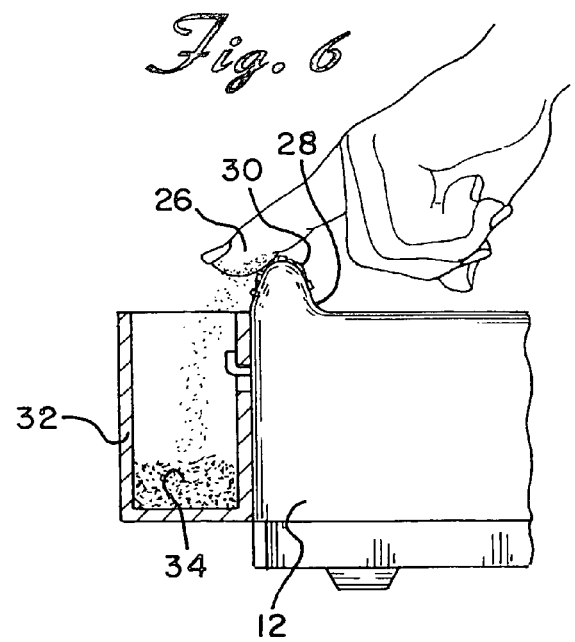
FIG. 6 illustrates a person using the device of the present invention in order to scrape off the cooled wax from his or her fingertip.

In order to use the device of the present invention, a quantity of wax 22 is placed into the container 24. The heating element 36 may be turned on and the temperature adjusted to the desired level. The wax will now be heated so that it is maintained in a molten state. The cover 14 is placed over the wax. (See FIG. 4.) A person may insert his or her fingertip 26 into the opening 20. (See FIG. 2.) In most cases, the person will touch the molten wax with only the pad of his or her fingertip as there is normally no reason to coat the fingernail, for example. The wax will harden onto the person's fingertip 26. When the person desires to remove the wax, he or she simply scrapes his or her finger along the edge 30 of the flange 28. The scraped wax 34 falls into the waste container 24. (See FIG. 6.) As the molten wax 22 is consumed, the cover 14 lowers by gravity. (See FIG. 5.) The quantity of wax 22 may be refilled as necessary.

The present invention may be placed adjacent any publicly used device and serves as a means for preventing the spread and contact of germs. For example, the present invention may be placed adjacent a touch screen 46 or key pad such as commonly found at a convenience store or ATM. (See FIG. 3.) A person's fingertip 26 need not come into direct contact with the screen 46 as the coating of wax 48 acts as a barrier between the screen 46 and the person's finger. Once the person has finished using the screen 46, the wax may be scraped off as described above.

The present invention may be embodied in other specific forms without departing from the spirit or essential attributes thereof and accordingly, reference should be made to the appended claims rather than to the foregoing specification as indicating the scope of the invention.

I claim:

1. A system for fingertip protecting that prevents the contact and spread of germs comprising:
    a housing having a container and a separate cover with an opening formed in said cover;
    a quantity of molten wax stored within said container, said molten wax having an upper surface;
    said cover resting on said upper surface of said molten wax, and
    means for heating said wax stored within said housing
    wherein a person's fingertip may contact said upper surface of said molten wax through said opening and wherein said cover is free to move downwardly within said housing as said wax is consumed.

2. The system of claim 1 further including means mounted on said container and separate from said cover for scraping hardened wax from the person's fingertip.

3. The system of claim 2 further including a waste container into which said wax scraping may be deposited.

* * * * *